United States Patent
Rosink (10) Patent No.: US 10,799,197 B2
(45) Date of Patent: Oct. 13, 2020

(54) ROUND FLAT DETECTOR FOR X-RAY IMAGING

(71) Applicant: KONINKLIJKE PHILIPS N.V., Eindhoven (NL)

(72) Inventor: Johannes Josephus Wilhelmus Maria Rosink, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/084,590

(22) PCT Filed: Mar. 7, 2017

(86) PCT No.: PCT/EP2017/055230
§ 371 (c)(1),
(2) Date: Sep. 13, 2018

(87) PCT Pub. No.: WO2017/157714
PCT Pub. Date: Sep. 21, 2017

(65) Prior Publication Data
US 2019/0076104 A1    Mar. 14, 2019

(30) Foreign Application Priority Data
Mar. 14, 2016 (EP) .................... 16160169

(51) Int. Cl.
*A61B 6/00* (2006.01)
*A61B 6/06* (2006.01)

(52) U.S. Cl.
CPC .............. *A61B 6/06* (2013.01); *A61B 6/4233* (2013.01); *A61B 6/4291* (2013.01); *A61B 6/4405* (2013.01); *A61B 6/4441* (2013.01)

(58) Field of Classification Search
CPC .................................................. A61B 6/4233
See application file for complete search history.

(56) References Cited

U.S. PATENT DOCUMENTS

| | | | | |
|---|---|---|---|---|
| 5,550,378 A | * | 8/1996 | Skillicorn | A61B 6/06 250/367 |
| 2004/0087852 A1 | * | 5/2004 | Chen | A61B 6/4405 600/407 |
| 2008/0078939 A1 | | 4/2008 | Hennessy | |
| 2013/0044860 A1 | | 2/2013 | Nicholson | |

FOREIGN PATENT DOCUMENTS

| | | |
|---|---|---|
| EP | 0051350 A2 | 5/1982 |
| EP | 1943950 A1 | 7/2008 |
| WO | 200042896 A2 | 7/2000 |

* cited by examiner

Primary Examiner — Dani Fox (57) ABSTRACT

An X-ray detector assembly (DA), comprising an X-ray sensitive flat panel (FD) module having a first shape. An X-ray shield (S) is superimposed on said panel, said shield having a hole i) of a fixed second shape different from said first shape or ii) of a fixed size different from a size of the first shape.

19 Claims, 4 Drawing Sheets

ROUND FLAT DETECTOR FOR X-RAY IMAGING

CROSS-REFERENCE TO PRIOR APPLICATIONS

This application is the U.S. National Phase application under 35 U.S.C. § 371 of International Application No. PCT/EP2017/055230, filed on Mar. 7, 2017, which claims the benefit of European Patent Application No. 16160169.5, filed on Mar. 14, 2016. These applications are hereby incorporated by reference herein.

FIELD OF THE INVENTION

The invention relates to an X-ray detector assembly, to a detector unit, to an X-ray imaging apparatus and to a method of assembling an X-ray detector assembly.

BACKGROUND OF THE INVENTION

Detector equipment for current X-ray imaging systems include image intensifier television systems (IITV) and more recent flat panel detector modules. The latter affords in general a better image quality (eg, has higher bit-depth) than IITV. In some imaging applications, such as in orthopedic imaging, it is customary to use IITV systems that have round or curved "look and feel" such as essentially round detector housings and that output round images. A set of protocol and workflow features have been built over the years that take advantage of this geometry.

SUMMARY OF THE INVENTION

There may therefore be a need for alternative imaging systems with improved image quality and that can be accommodated to legacy workflow features.

The object of the present invention is solved by the subject matter of the independent claims where further embodiments are incorporated in the dependent claims. It should be noted that the following described aspect of the invention equally applies to the detector unit, to the X-ray imaging apparatus and to the method of assembling an X-ray detector assembly.

According to a first aspect of the invention, there is provided a mobile X-ray imaging apparatus comprising an X-ray detector unit having a housing and an X-ray detector arrangement. The detector arrangement further comprises an X-ray sensitive flat panel module having a first shape and an X-ray shield superimposed on said module. The X-ray shield has a hole of a fixed second shape different from said first shape. A shape of said housing conforms to said second shape.

According to one embodiment, said second shape is curved. More particularly, in one embodiment, said second shape is essentially circular. According to one embodiment, the first shape is essentially rectangular, in particular square. Especially the square shape for flat panel modules allows relatively low manufacturing costs.

According to one embodiment, said shield is configured and superimposed so as to cover at least one corner portion of the flat panel module.

According to one embodiment, the hole is so formed that the second shape osculates the first shape at at least one location. This affords a more compact design and tighter packing.

According to one embodiment, a shape of said housing conforms is curved (in particular circular or oval), at least when viewed in plan view along an optical axis of the detector unit. Yet more particularly, and in one embodiment, the housing is essentially a cylinder.

According to one embodiment, said shield is mounted on said panel or wherein said shield is mounted inside or outside the housing, opposite a radiation ingress window of said housing.

According to one embodiment, the imaging apparatus is configured for orthopedic imaging. In particular, a diameter of the housing is 25-40 cm, in particular about 30 cm, more particularly about 32 cm. Other imaging applications such as vascular are also envisaged.

According to one embodiment, the apparatus is of the mobile type. That is, the apparatus can be moved essentially as is (without requiring disassembling) into another room.

The X-ray shield essentially transforms a field of view for the detector module from the first to the second shape. In addition, the shield helps to reduce incurring radiation dosage outside the radiation sensitive surface. Specifically, the shield is configured to comply with primary protective shielding requirements as laid out in in to IEC60601-2-54 (ed. 1.1), clause 203.11.

In particular, in the proposed imaging apparatus, a round or curved housing and image format may be combined with rectangular/square flat panel technology. Thus, better image quality may be achieved than when using a conventional mobile apparatus with an IITV-based detector arrangements. In particular, flat panel technology may be used with a mobile imaging apparatus without requiring any changes in current workflow or image processing. Thereby, a detector module substrate (glass plate or silicon wafer) can remain square or rectangular, so that current state-of-the-art manufacturing and readout electronics are available.

Further, for example, existing IITV-based mobile imaging systems may be retrofitted with flat panel detector technology in an efficient and straightforward manner.

In particular in orthopedic imaging, the, compared to IITV systems, reduced thickness (in direction of the optical axis) affords the advantage of direct line-of-sight between a surgeon and an operator of the X-ray imaging apparatus (in particular, C-arm).

Application of the proposed mobile X-ray apparatus include in particular orthopedic imaging but other use cases are also envisaged, such as vascular imaging, including subtraction/DSA (digital subtraction angiography) imaging.

The term "superimposed" herein is to mean that, during use of the detector assembly in the X-ray imaging apparatus, the shield is located between the flat panel detector module and the X-ray source of the imaging apparatus. The term "superimposing" includes "mounting on" but it also includes that the superimposing is effected only when the assembly is introduced into the housing or, more generally, in the detector unit, where the shield is pre-installed. Superimposing or "mounting (on)" includes the two components shield and flat panel module are urged into contact with each other, however this is not necessarily so as in alternative embodiments the two components are merely coupled to each other via one or more intervening layers/components. Also, superimposing can also be achieved at a distance, that is, there is a gap/clearance filled with air or a liquid between the shield and the flat panel module so the two components may still not be in physical contact with each other, even though there is no intervening component(s).

BRIEF DESCRIPTION OF THE DRAWINGS

Exemplary embodiments of the invention will now be described with reference to the following drawings wherein.

DETAILED DESCRIPTION OF EMBODIMENTS

Figure 1:
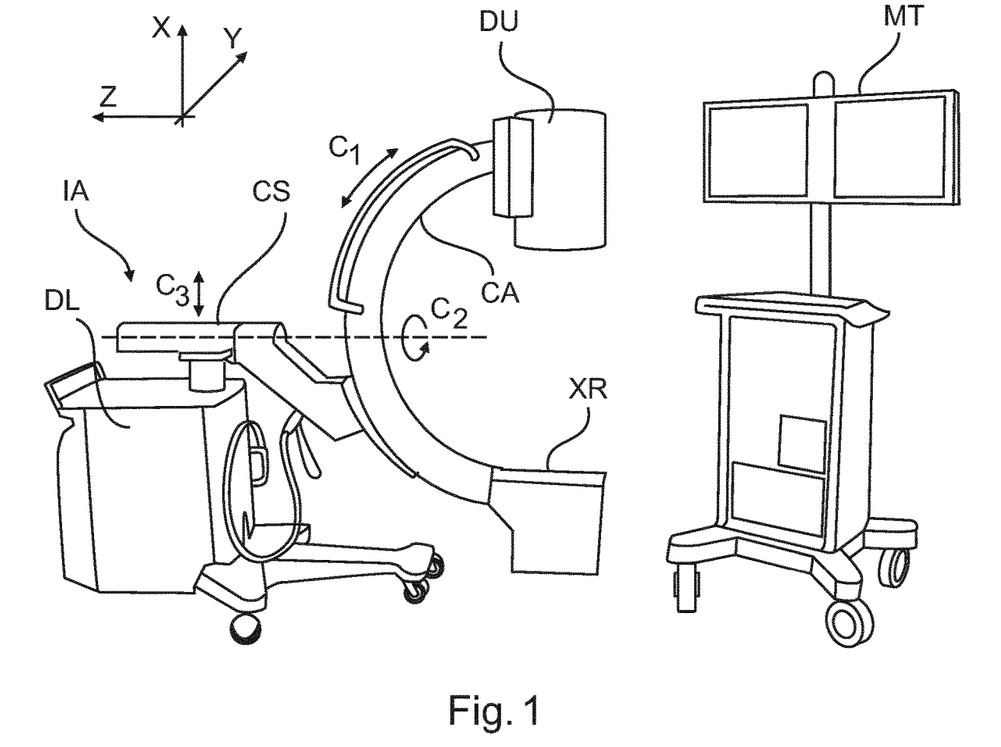
FIG. 1 shows an X-ray imaging apparatus.

FIG. 1 shows a schematic diagram of an imaging arrangement IMA. The imaging arrangement IMA comprises a rotational X-ray apparatus ("imager") IA and a system SIA for supporting operation of imager IA.

Turning first to the imager IA, this includes one or more imaging components IC. The imaging components include an X-ray source XR and an X-ray sensitive detector unit DU. In one embodiment the rotational X-ray imager is of the C-arm or U-arm type. A combined imaging component is defined in these types of imagers where the X-ray source and the detector are connected in a stiff C-arm or U-arm structure. The C-arm CA is rotatably supported in a cradle structure CS.

As the name suggests, in these type of imagers the C-arm or U-arm is a gantry having the shape of a turned over letter "C" (or "U"). The imaging components, that is, the X-ray source XR and the detector D, are respectively, connected to the respective ends of the C-arm. In this manner the gantry CA embraces at least partly an imaging region and has the X-ray source and the detector arranged in opposed relationship across said imaging region.

Optionally, the imaging arrangement IA further includes in one embodiment an object support, such as a patient table (not shown). The object support supports an object to be imaged during the imaging procedure. In one embodiment, but not necessarily all embodiments, a medical context is envisaged where the "object" is a patient PAT or at least a part of the patient's anatomy. Human or animal patients are envisaged herein. The object however may also be inanimate such as an item of baggage in screening applications or the object may be a sample in non-destructive application, etc. Although in the following we will refer mainly to the medical context, this is not to exclude these (and other) non-medical contexts. The table however is optional as the imager may also be used whilst the patient is standing.

The image apparatus IA in FIG. 1 shows a mobile solution with the cradle structure mounted in a moveable dolly structure DL. However this is exemplary, as fixed solutions are also envisaged where the C-arm is rotatably ceiling, floor or wall mounted or mounted on a cradle fixedly connected to the ground GR of the imaging venue (examination room, etc).

The imaging apparatus enjoys a number of different mechanical degrees of freedom to help a user achieve best imaging results (by "user" we refer to the person operating the imager). For instance, and as shown in FIG. 1, the combined imaging component (that is, the C-arm with the source XR and detector D connected therein) is rotatable not only about a single, but two or more rotation axes although embodiments with a single rotational degree of freedom are not excluded herein.

One rotation axis is shown in FIG. 1 as a dashed line. It allows rotation essentially about the longitudinal axis of the patient when lying on the patient table. This first rotation is indicated by C2 in the Figure.

There is also another rotation envisaged herein referred to in the following as "angulation". This rotation is around an axis Y which extends perpendicular into the plane of the drawing of FIG. 1. That is, the axis for the angulation is perpendicular to the longitudinal axis of the patient. The angulation is shown as C1. In addition to having the one or more rotation axis, the cradle structure is height adjustable relative to ground GR. In some embodiment the cradle can be moved sideways (in and out of the drawing plane as per FIG. 1) in an arc. In one embodiment, the arc spans about 10-20 degrees but these angular figures are merely exemplary.

The respective translations or rotations (in particular the angulation) are brought about by suitable actuators (not shown) such as stepper motors or servo motors suitable arranged and controlled from an operator console CON. The console CON includes one or more user control interfaces such as a joystick, foot pedal or other. When the user, such as an interventional radiologist, operates the user interface of the console, a series of commands are issued. These are translated into electrical control signals with which the various actuators can be controlled and adjusted. Broadly, during the imaging procedure, the user requests a certain imaging geometry by operating the console and issues the control signals to the respective actuators. In response thereto it is in particular the C-arm's angulation and/or height that are adjusted to achieve the best possible view of the anatomy of interest. Once the desired imaging geometry is assumed, that is, once the C-arm has moved into place, the X-ray source is operated to emit an X-ray radiation beam which passes through the anatomy of interest. The X-ray beam interacts with matter in the anatomy. The interacting X-rays emerges at the far end (relative to the X-ray source) from the patient and then impinge on an X-ray sensitive surface in the detector unit DU. The surface is made up from detector pixels that produced digitized image signals which can be processed into images. The images can then be rendered for display on a display unit (monitor, etc) MT to so support the user. It should be understand, that all of the above is of equal application to manual systems, without actuators. In these embodiments, the C-arm is moved manually by the user. The X-arm may be provided with handle and grip options to facilitate this.

Figure 3:
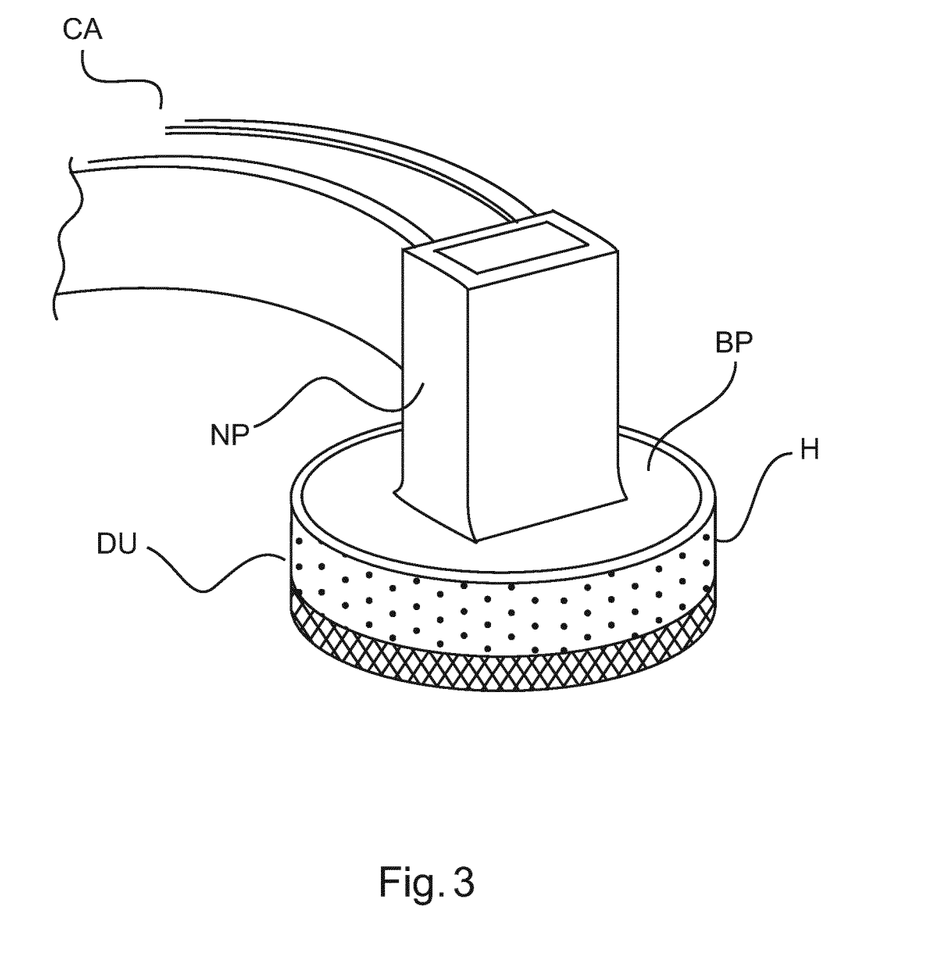
FIG. 3 shows a close up of a detector unit attached to a gantry.

With reference to FIG. 3, this is a close-up in perspective view of the end of the C-arm CA where the detector unit DU attaches. More particularly—the C-arm transitions into a neck portion NP. The neck portion transitions into a mounting plate BP. The detector unit comprises a detector assembly DA (see FIG. 4) and an outer housing H. Specifically, the mounting plate carries the detector assembly housed in the housing H which attaches to the mounting or mounting plate BP to cover the detector assembly DA. The neck portion is optional.

The neck portion NP, if any, and the C-arm CA are hollow structures so that cable work to and from the detector unit DU can be routed there-through to supply electricity to the detector unit and/or for transferring image information collected at the unit DU. The mounting plate has one more holes to afford passage of said cable-work from the detector assembly DA.

As can be seen, the detector unit DU has in general a curved, in particular round, shape. Yet more particularly and according to one embodiment, but not necessarily all embodiments, the detector unit DU is essentially cylindrical. Yet more particularly, the housing H is cylindrical. It has an opening at one end so as to be receivable by the mounting plate. In this embodiment, the mounting plate BP is disc shaped so as to accurately register with the circular opening of the housing. In general the shape of the mounting plate conforms to that of the housing so may or may not be circular depending on the overall shape of the detector unit DU and hence the housing H. The hollow space between the outer housing (shell) H and the mounting plate BP so formed is sized so as to accommodate the detector assembly DA.

Figure 4:
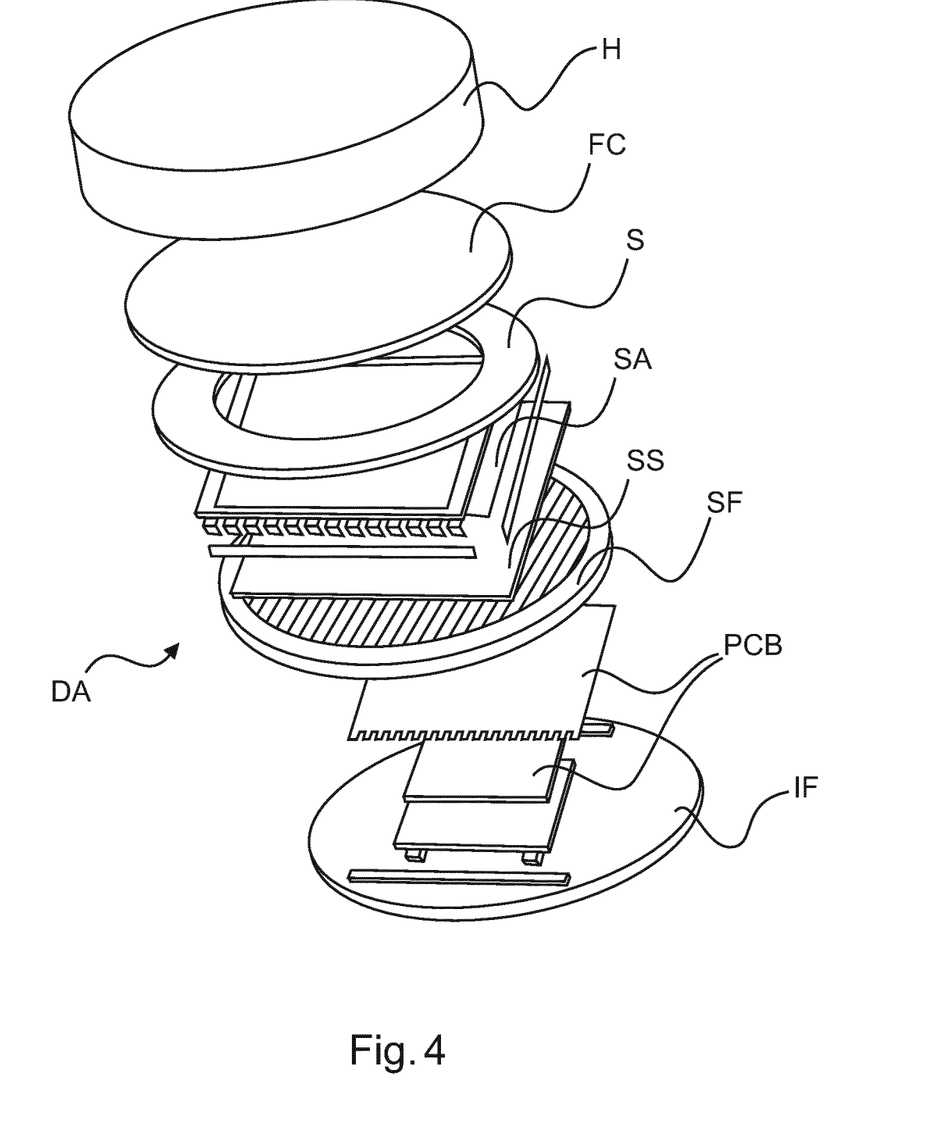
FIG. 4 shows an exploded view of the assembly with a housing.

The mounting plate BP and details of the detector assembly DA are shown in exploded view in FIG. 4 to which reference is now made.

The detector assembly DA has in general a layered structure comprising a plurality of stacked components.

Progressing from the detector housing H in a direction away from the X-ray source and towards the mounting plate BP, there is an optional, internal front cover FC which is overlaid on an annular protective shield or barrier of curved shape that corresponds to the round shape of the detector unit. The protective shield S is formed from lead, tungsten or other suitable high Z-material or a suitable alloy. In one embodiment, the maximum allowed air kerma behind the shield is 150 uGy per hour. Border(s) of the annular protective shield is hence essentially X-radiation opaque and X-radiation can only pass unhindered through its hole or cutout.

The shield S is overlaid or superimposed on a flat panel detector module FD. The flat panel FD comprise a sensor assembly SA and a sensor substrate SS. The sensor assembly is carried by the sensor substrate SS (glass or silicon substrate or other). The shield S partly extends into and thus overlays portions of a radiation sensitive surface of the sensor assembly SA. The radiation sensitive surface is arranged proximal to the radiation source. The radiation sensitive surface is in general rectangular, in particular square shaped and not round as the shield's hole, on which more further below at FIG. 5.

The radiation sensitive surface is made up from pixel elements arranged in an array or "matrix". The pixel elements operate to convert impinging X-radiation into respective electrical signals. The sensor assembly SA may be any one of the indirect or direct conversion type. In the indirect conversion type, the radiation sensitive surface is essentially a matrix of thin film transistors formed as a matrix pattern in a silicon-on glass layer (eg, amorphous Silicon, LTPS (Low-temperature polycrystalline silicon), IGZO (Indium gallium zinc oxide), or other). Each transistor defines a pixel. A scintillator layer converts impinging X-ray into light, and this is in turn converted into the respective electrical signals, thus indirect conversion. In the direct type, the radiation sensitive layer is formed from amorphous selenium (or other suitable material on a substrate), that directly converts X-ray photons into an electric charge. The electrical signals are essentially electron-hole recombination charges, and these are registered by a matrix of TFTs defining the pixels.

In either of these embodiments, that is, direct or indirect type, the electrical signals at the pixels are routed via read-out conductor lines from the pixels to the respective edges of the sensor assembly. The read-out conductor lines are generally run in a grid pattern across the radiation sensitive surface.

The housing H has a radiation ingress window on the side facing the X-ray source. The ingress window is arranged essentially opposite the optional internal cover FC and the said radiation sensitive surface of the flat panel FD. The ingress window and the optional internal front cover are essentially X-radiation transparent so the X-ray radiation is only negligibly modified (if at all) when passing thereto and onto the radiation sensitive surface. As briefly mentioned, the flat panel FD, in particular its sensor assembly, and more particular the shape of the radiation sensitive surface is preferably square or rectangular. Other shapes are not excluded per se, however current sensor manufacturing techniques allow manufacturing for rectangular, in particular square shapes, at low cost.

As shown in FIG. 4, the rectangular flat panel FD includes, at at least two of its edges, read-out circuitry for receiving the read-out conductor lines. The read-out circuitry processes the electrical charge signals generated at the pixels. The read-out circuitry is electronically coupled to one or more PCBs arranged further down in the stack. The PCBs include circuitry to process signals received from the read-out circuitry. To forward the signals, the PCBs are coupled to the cable-work which runs through the mounting plate PB and the neck portion NP and eventually through the C-arm CA as mentioned above when describing FIG. 2.

Optionally, and further down in the stack, preferably between the flat panel FD and the PCBs, there is a sub-frame SF which itself includes lead shielding. This is to further protect in particular the electronic circuitry on the PCBs from X-radiation exposure, although part of this function is also performed by the shield S on top of flat panel FD. The shape of the sub-frame SF may conform to that of the housing of shield S (as shown) or may conform to the shape of the sensor assembly AS, so may in particular be square/rectangular. To protect the flat panel read-out circuitry from radiation, this is arranged behind the shield S and folded around the flat panel FD towards the back of the panel where it is connected to processing circuitry on the PCBs. Same or all PCBs may conform in shape to the shield/housing or to the flat panel. In particular, the PCBs may be round or rectangular (specifically, square) in different embodiments.

Optionally, the above described component stack are packaged into a single internal housing, sealed off with a front cover FC on the X-ray source XR proximal side and an interface frame on the side distal to the X-ray source XR. The interface frame IF is configured for connection with the mounting plate PB. The detector assembly package is connectable as a whole via the interface frame to the mounting plate and is suitably affixed thereto (screwed, bolted, glued or otherwise). Having the detector assemblies arranged in a package as described, allows improved dust protection and better handling, eg for maintenance. Still, alternatively, the individual components are each secured to each other and then to the mounting plate or each or some of the components are individually secured to the mounting plate PB. It will be appreciated that the order of the component in the stack as per FIG. 4 is but one embodiment, and variations in this order are also envisaged herein.

Figure 2:
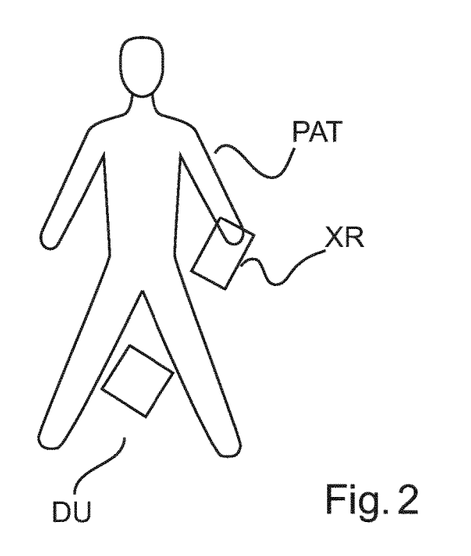
FIG. 2 shows an imaging scenario using an X-ray imaging apparatus.

Having a round, or at least a curved, detector housing as proposed herein is particularly advantageous for certain imaging applications such as in orthopedics or others. This is illustrated in FIG. 2 which shows a plan view on the X-ray imaging arrangement along negative X direction and on the patient lying on patient table. In FIG. 2, the C-arm CA (which is not shown to avoid cluttering) has been angulated by about 90° around Y axis as compared to the configuration as per side elevation view in FIG. 1. In the configuration of inset FIG. 2B, the X-ray source XR is now positioned close to the patient PAT hip whilst the detector unit DU is positioned between the patient's leg. This imaging scenario may be used in orthopedic applications to image for hip fracture for instance. As will be appreciated, in these imaging scenarios, having a round/curved detector housing will make the imaging experience more convenient for the user's workflow. For instance, in orthopedic imaging, it is easier for the user to position the detector correctly between the patient's legs, and so to optimize user's workflow.

Reference is now made to FIG. 5A which shows a plan view on the square shaped flat detector panel of FIG. 4, with the annular protective shield S overlaid thereon. As mentioned earlier, unlike in previous constructions which also use shield barriers, this kind of shield S extends into the radiation sensitive area or surface of the flat panel FD. In particular, corner portions are covered by the shield as shown in hachures in FIG. 5A.

One function of the said shield is to transform a shape of a native field of view of the flat panel detector into a different field of view as defined by the shape of the shield's radiation passage hole. Specifically, the field of view can be made to correspond to the shape of the housing as in the embodiment in FIG. 3, where a round housing is used, housing a rectangular flat panel, and the detector unit DU produces round pictures thanks to the annular shield superimposed on the flat panel module. This is achieved by ensuring the shape of the shield's hole has the desired or target shape for the field-of-view (FOV) and by having the shield partly extend over the radiation sensitive area to essentially disable unwanted portions of the radiation sensitive area. The FOV describes the maximum size/dimension of an anatomy that can be wholly captured by the sensor assembly in an image.

Another function of the shield is to reduce or limit residual radiation, that does not fall directly onto the flat panel FD Specifically, x-radiation that happens to fall outside the laterally flat panel's sensitive surface/area is absorbed by the shield. Specifically, size and shape and material of the shield is configured to absorb unwanted radiation that does not impinge on the radiation sensitive area, such as that part of the primary beam that falls outside the flat panel area (primary beam is that part of the radiation beam that does not comprise scatter radiation). Compliance with this requirement can be tested by placing an X-ray dosimeter behind the detector unit DU. Ideally then no or merely negligible radiation should be registered by the dosimeter.

Generally, what is proposed herein in one embodiment is that the passage hole in shield S has a different shape than the radiation sensitive surface. In sum, the shield with the passage hole has a dual function: i) to reduce/absorb lateral radiation around the flat panel detector (in particular as per IEC60601-2-54 mentioned above) and ii) to transform native FOV shape of the flat panel detector into a different shape.

In the proposed system, a round FOV can be achieved without re-routing the read-out lines or having readout lines (also referred to as "rows and columns") run at different lengths, thus saving manufacturing costs. The unwanted pixels are simply eliminated as it were by overlaying the shield over the unwanted portions (such as the corner portions of the radiation sensitive area).

FIG. 5A shows a specific example: The overall outer diameter of the outer housing H is about 30 cm, in particular 32 cm. The protective annular shield is arranged in front of the flat panel, proximal to the X-ray source XR, thus defining a new FOV shape. The shield S has a radial thickness of its border portion of about 4.5 cm to so extend into the radiation surface to cover the corner portions CP of the radiation sensitive area. At the same time the shield extend beyond, to the outside, of the image sensitive area by at least 2 cm or 3 cm as defined in IEC 60601-2-54. The covered corner portions CP have the shape of triangles (shown in right-sloping hachures) with a curved edge but this will depend on the geometry of the passage hole and the native shape of the radiation sensitive area. The hole CO of the annular shield S then defines a new shape (round that is) as "cut out" as it were from the original native square shape of the radiation sensitive surface. The new, in this case round, FOV has, in the exemplary embodiment of FIG. 4A, a size of about 21 cm×21 cm which is comparable to the size of a FOV of a round 9" intensifier screen IITV (image intensifier television), which is shown in comparison in FIG. 4B. The corners of the flat panel may be rounded to facilitate better fit in a compact round housing H.

In a prior art IITV detector module as shown in FIG. 5B, it is of note that the shielding does not extend into the radiation sensitive area but merely skirts it. It will be appreciated, that the embodiment of FIG. 5A allows achieving the same "look and feel" as traditional 9" IITVs. Even the housing may be dimensioned as a traditional 9" IITV housing. In other words, work-flow etc can remain as it always was in IITV, but with the added benefit of better image quality thanks to the flat panel module instead of image intensifier technology.

It will be appreciated that in order to maximize the field of view, that the hole's shape is so configured as to osculate the shape of the radiation sensitive area at at least one location.

In the embodiment shown in FIG. 5A, a square radiation sensitive area is combined with a circular hole, whereby a diameter of the hole corresponds to a length of each side of the radiation sensitive area. Thus, the hole and the radiation sensitive area touch at 4 locations in the middle of each side of the radiation sensitive area, each indicated by 'x'.

In other examples, osculating may not necessarily be achieved at all edges for instance, if the panel FD is not a square but a more general rectangle. However, osculating at all edges can still be achieved when configuring an oval or elliptic hole with minor/major axes corresponding in length to the two different edge sizes of the FD panel. In the alternative to this osculating configuration, the shield extends radial further into the radiation sensitive area, thus defining an additional shielding region between the hole's edge and the respectively neighboring edge of the panel. This additional shielding region can be used to accommodate the read-out circuitry of the panel FD and at the same time protect same from radiation. In some embodiments, it may be sufficient to choose the size and shape of the shield such that its outer perimeter forms a convex hull of the outer perimeter of the radiation sensitive area as shown in FIG. 5A in left slopping hachures. In other embodiments the shield is larger than the geometric convex hull of the radiation sensitive area. The outermost, right-sloping hachures in FIG. 5A illustrate an interspace between the shield S and the surrounding housing S. This affords extra protection from lateral radiation around the radiation sensitive area. In general, the overall size of the shield is chosen to comply with requirements as laid down in IEC 60601-2-54, edition 1.1, 2015 or equivalents.

It will be appreciated that the protective shield allows transforming in particular the shape of the native shape of the flat panel FD's radiation sensitive surface without collimator equipment. In particular, and compared to a collimator, the shape of the shield's hole is fixed and cannot be changed for a given detector, although different shields can be used at the manufacturing stage for detectors of different shapes and sizes. This increases user's safety.

The shield is generally symmetric with the hole being positioned around the shield's center, such as in the circular annular embodiment. Annuli other than circular, such as polygonic, etc, are also envisaged. Alternatively, asymmetric arrangements are also envisaged. For instance, the shield S's hole may be arranged off-center. In addition or instead, the center point of the flat panel FD and the center point of the shield S are not coincident but shifted relative to each other, but by an amount small enough so that the flat panel FD's corners are still covered by the shield S.

Figure 5:
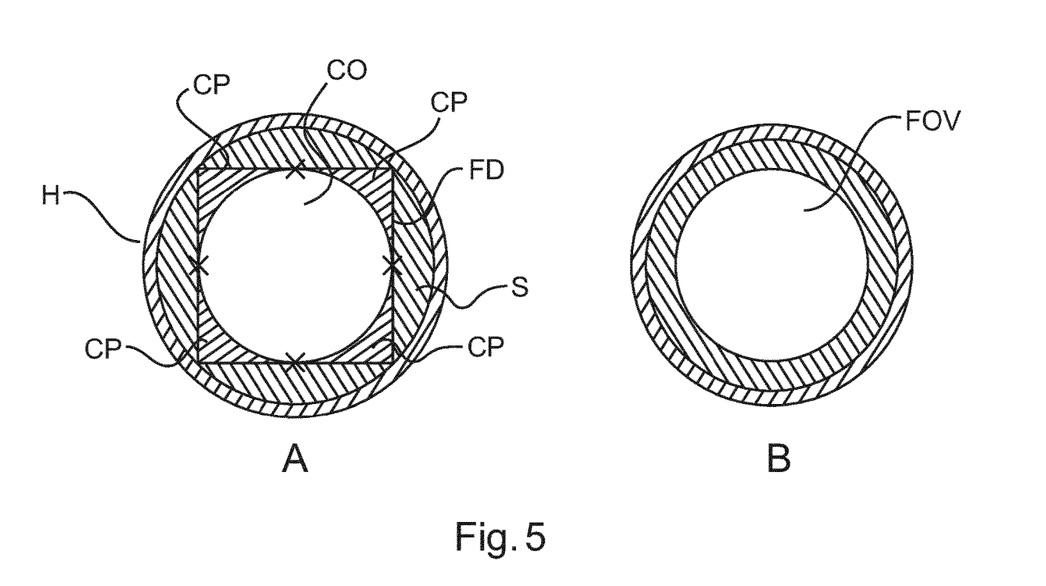
FIG. 5 shows plan views of the detector assemblies.

As shown in FIGS. 4,5, in a preferred embodiment the shield is fixedly (releasably or, preferably, permanently) mounted on the flat panel module FD to form a double-decker structure. This can then be mounted as a whole into the detector housing as shown in FIG. 4. However, in an alternative embodiment the shield S is not mounted as such on the flat panel module FD but is instead mounted inside the housing H, opposite and under the ingress window of the housing H. The super-positioning of the shield with the flat panel is then achieved when the flat panel is mounted on the mounting plate and when the housing is put into place. In another embodiment, although less preferable, the shield S may also be mounted on the outside of the housing around the ingress window and again comes to be superimposed on the flat panel upon mounting the flat panel onto the mounting plate BP and upon applying the housing to the mounting plate BP thus positioning the shielding so as to achieve the superimposing with the flat panel FD. Alternatively, the shield may be arranged in a swivel or revolving mechanism attached to the mounting plate rather than the housing, which can be swung and locked into place so as to superimpose the flat panel module after the flat panel module has been mounted to the mounting plate.

Although in the previously above described embodiments, the two shapes involved were square shape or rectangular shape for the flat panel and circular shape for the shield's S hole CP, different shapes may be used in different embodiments. For instance, the shield may not be circular but oval or may be a semi-circle or other curved structure whilst the flat panel may have a shape other than rectangular.

In yet another embodiment, the shape of the shield's S hole CP and the shape of the flat panel may still be the same but at different sizes. In other words, in one embodiment the flat panel may be rectangular as shown in FIG. 4A and so is the shield's hole, but smaller. Specifically, the shielding's border area still extends into the radiation sensitive surface of the panel so as to transform the original rectangular field of view into a smaller rectangular field of view. The covered pixel portions may still be used for calibration purposes to compensate for offset, drift, gain, etc. This may allow help to decrease image noise or similar. Again, shapes other than rectangular may be transformed into smaller ones in this embodiment.

Figure 6:
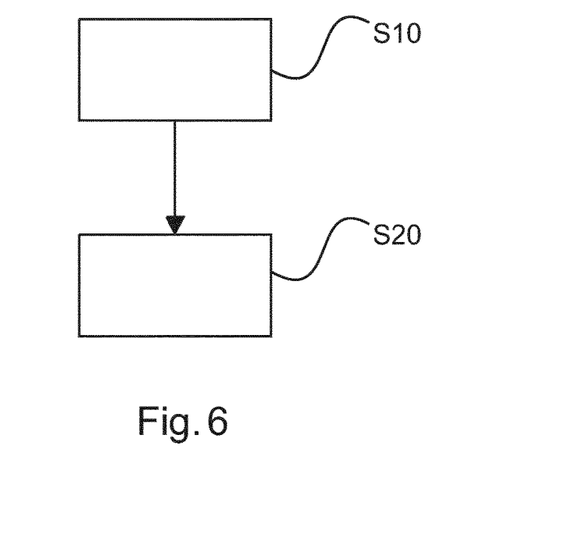
FIG. 6 shows a flow chart for assembling a detector assembly.

Reference is now made to FIG. 6, showing a flow chart for a method of assembling an X-ray detector assembly DA.

At step S10, a flat panel module is provided having an x-radiation sensitive surface of first shape, such as square or rectangular or other.

In step S20, a shield with a hole, which serves as a lateral protective barrier to absorb unwanted radiation in the periphery of the flat panel, is superimposed on the flat panel to so obtain a detector assembly having a double-decker structure. "Superimposing" as used herein means that, when the detector assembly is in use in an X-ray imager, the shield is situated between the panel FD and the X-ray source XR.

The flat panel has a shape which is different from the shape of the shield's hole. In a preferred embodiment, whilst the shape of the flat panel is rectangular or square, the shield's hole has a curved, such as a round or oval shape, to define a new FOV (field of view) of the flat panel module whose shape if different from the native FOV of the panel FD. In particular, a curved field of view is achievable when the detector assembly is used in imaging. In other words, the shield allows transforming a native FOV of the flat panel module FD into a new shape defined by the geometry of the hole in the shield.

The shield is formed from an x-radiation blocking material such as lead or other or an alloy. The shield may be a formed as a monolithic structure such as by stamping out from a sheet of lead or tungsten. Alternatively, the shield may be assembled from discreet pieces such as two or more semi-arches which are joined at their respective ends by soldering, gluing or are otherwise affixed to each other. The later approach, although more involved, allows making more efficient of the sheet material than stamping.

In one embodiment, the step of superimposing the shield onto the radiation sensitive area of the panel module DF is achieved by mounting the shield onto the panel by gluing, screwing, bolting, welding, soldering, etc. Preferably, the shield is permanently bonded to the flat panel FD but solutions where the mounting is releasable are also envisaged in some embodiments.

Alternatively, rather than forming the detector assembly by combining the shield with the flat panel into a single (sub-)unit, the superimposing is not achieved before mounting the detector assembly in the housing of the detector unit. In other words, in this alternative embodiment, the superimposing is achieved only upon insertion of the detector assembly, in particular the flat panel, into the detector unit, in particular into said housing. In other words, the superimposing is achieved only "in-situ" on the spot. This can be implemented by pre-installing the shield into the housing for instance either inside or outside. When the detector assembly including the flat panel module is then mounted in the imaging system (eg, on a mounting plate) and the housing is then applied to cover the detector assembly, only then is the superimposing effected. Alternatively, the shield may be arranged on a swivel mechanism attached to the mounting plate rather than the housing, which can be swung into place so as to superimpose the flat panel module after the flat panel module has been mounted to the mounting plate.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features. While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an"

does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mobile X-ray imaging apparatus comprising:
   an X-ray detector unit having a housing; and
   an X-ray detector arrangement comprising:
      an X-ray sensitive flat panel detection module comprising a sensor substrate and a sensor assembly with a radiation sensitive surface having a first shape;
      a protective shield superimposed on the X-ray sensitive flat panel detection module, the protective shield having a hole of a fixed second shape different from said first shape,
      wherein a shape of the housing conforms to the second shape, and
      wherein the protective shield overlays portions of the radiation sensitive surface of the sensor assembly.

2. The X-ray imaging apparatus of claim 1, where the second shape is curved.

3. The X-ray imaging apparatus of claim 1, where the second shape is essentially circular.

4. The X-ray imaging apparatus of claim 3, wherein the first shape is essentially rectangular or square.

5. The X-ray imaging apparatus of claim 1, wherein the protective shield is configured and superimposed so as to cover at least one corner portion of the flat panel module.

6. The X-ray imaging apparatus of claim 5, wherein the hole is so formed that the second shape osculates the first shape at at least one location.

7. The X-ray imaging apparatus of claim 1, wherein the protective shield is mounted on the X-ray sensitive flat panel detection module.

8. The X-ray imaging apparatus of claim 1, further comprising a rotational X-ray imager for orthopedic or vascular imaging.

9. The X-ray imaging apparatus of claim 1, wherein the housing comprises a radiation ingress window, and
   wherein the protective shield is mounted inside or outside the housing, opposite the radiation ingress window.

10. An X-ray detector for a mobile X-ray apparatus, comprising:
    an X-ray sensitive flat panel detection module comprising a sensor substrate and a sensor assembly with a radiation sensitive surface having a first shape; and
    a protective shield superimposed on the X-ray sensitive flat panel detection module, the protective shield having a hole of a fixed second shape different from the first shape, wherein the protective shield overlays portions of the radiation sensitive surface of the sensor assembly,
    wherein the second shape is selected to conform to a shape of a housing of a detector unit of the mobile X-ray apparatus.

11. The X-ray detector of claim 10, where the first shape is square or rectangular.

12. The X-ray detector of claim 11, wherein the second shape is circular or oval.

13. The X-ray detector of claim 12, wherein the hole of the second shape osculates the first shape.

14. An X-ray detector for a mobile X-ray apparatus, comprising:
    a housing;
    an X-ray sensor assembly positioned within the housing, the sensor assembly comprising a radiation sensitive surface having a square or rectangular shape; and
    a protective shield superimposed on the sensor assembly within the housing, the protective shield defining a hole having a circular or elliptical second shape,
    wherein the protective shield overlays a portion of the radiation sensitive surface, and the hole defined by the protective shield exposes another portion of the radiation sensitive surface for receiving X-ray radiation, transforming a field of view for the X-ray detector from the square or rectangular shape to the circular or elliptical shape.

15. The X-ray detector of claim 14, wherein the housing has the circular or elliptical shape.

16. The X-ray detector of claim 14, wherein the hole osculates at least one side of an outer perimeter of the radiation sensitive surface.

17. The X-ray detector of claim 16, wherein a diameter of the hole corresponds to a length of each side of the outer perimeter of the radiation sensitive surface.

18. The X-ray detector of claim 14, further comprising:
    a front cover within the housing proximal to an X-ray source; and
    an interface frame distal to the X-ray source, wherein the protective shield and the X-ray sensor assembly are stacked in order between the front cover and the interface frame.

19. The X-ray detector of claim 14, wherein the protective shield comprises at least one of lead and tungsten.

* * * * *